(12) United States Patent
Bosch et al.

(10) Patent No.: US 7,232,927 B2
(45) Date of Patent: Jun. 19, 2007

(54) PREPARATION OF MONO-N-SULPHONYLATED DIAMINES

(75) Inventors: Boris Elmar Bosch, Köln (DE); Frank Gerhartz, Leverkusen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 74 days.

(21) Appl. No.: 10/463,799

(22) Filed: Jun. 17, 2003

(65) Prior Publication Data

US 2005/0059842 A1    Mar. 17, 2005

(30) Foreign Application Priority Data

Jun. 17, 2002 (DE) .............................. 102 26 944

(51) Int. Cl.
C07C 211/00 (2006.01)
C07C 273/00 (2006.01)
(52) U.S. Cl. ........................................... 564/1; 564/61
(58) Field of Classification Search ................. 502/155; 564/1, 61
See application file for complete search history.

(56) References Cited

U.S. PATENT DOCUMENTS 6,184,381 B1 * 2/2001 Ikariya et al. .............. 546/136
6,887,820 B1 * 5/2005 Ikariya et al. .............. 502/155

OTHER PUBLICATIONS

Balsell, Jaume et al.: J. Org. Chem., Bd., 65, 2000, Seiten 5005-5008, XP002261976 *Seite 5005-Seite 5007.

Balsells, Jaume et al.: Tetrahedron-Asymmetry, Bd. 9, 1998, Seiten 4135-4142, XP0001091305 *Seite 4136* *Seite 4138*.
Ng K et al: "Synthesis of homochiral pentadentate sulfonamide-based ligands" Tetrahedron: Asymmetry, Elsevier Science Publishers, Amsterdam, NL, Bd. 12, Nr. 12, Jul. 16, 2001, Setien 1719-1722, XP004298252 ISSN: 0957-4166 *Seite 1719-Seite 1720*.
Meuzelaar G et al: "Chemistry of Opium Alkaloids, 45. Improvements in the Total Synthesis of Morphine" European Journal of Organic Chemistry, Wiley-VCH Verlag, Weinheim, DE Bd. 9, 1999, Seiten 2315-2321, XP002192470 ISSN: 1434-193X *Seite 2317* *Seite 2319-Seite 2320*.
Zassinovich et al., Chem. Rev. (month unavailable) 1992, 92, 1051-1069 "Asymmetric Hydrogen Transfer Reactions Promoted by Homogeneous Transition Metal Catalysts".
Wills et al., Tetrahedron, Asymmetry 10, (month unavailable) 1999, 2045-2061, "Asymmetric transfer hydrogenation of C=O and C=N bonds".
R.A. Sheldon et al., Eur. J. Org. Chem. (month unavailable) 1999, 2315-2321, "Chemistry of Opium Alkaloids, 45[‡]Improvements in the Total Synthesis of Morphine".
Noyori et al., J. Amer. Chem. Soc. (month unavailable) 1995, 117, 7562, "Asymmetric Transfer Hydrogenation of Aromatic Ketones Catalyzed by Chiral Ruthenium(II) Complexes".
Noyori et al., American Chemical Society, Accounts of Chemical Research, vol. 30, No. 2, (month unavailable) 1997, 97-102, "Asymmetric Transfer Hydrogenation Catalyzed by Chiral Ruthenium Complexes".

* cited by examiner

Primary Examiner—Samuel A Barts
Assistant Examiner—Lalitha Nagubandi
(74) Attorney, Agent, or Firm—Michael A. Miller

(57) ABSTRACT

The present invention relates to a process for preparing mono-N-sulphonylated diamines by reacting diamines with sulphonyl halides in the presence of water, base and organic solvents.

11 Claims, No Drawings

PREPARATION OF MONO-N-SULPHONYLATED DIAMINES

BACKGROUND OF THE INVENTION

1. Field of the Invention

The present invention relates to a process for preparing mono-N-sulphonylated diamines by reacting diamines with sulphonyl halides in the presence of water, base and organic solvents.

2. Brief Description of the Prior Art

Mono-N-sulphonylated diamines, especially in optically active forms, have gained high industrial significance, for example, as ligands in catalysis (see, for example, Noyori et al. J. Amer. Chem. Soc. 1995, 117, 7562).

The preparation of mono-N-sulphonylated diamines is known in principle. For example, R. A. Sheldon et al., Eur. J. Org. Chem. 1999, 2315 describe their preparation from diamines using sulphonyl halides in the presence of triethylamine.

However, a disadvantage of this process is that mixtures of unsulphonated, mono-N-sulphonated and di-N-sulphonated products are formed which have to be subjected to a complicated chromatographic separation (see also EP-A 1 174 426). In the existing processes, the selectivities range from 30 to 85%, based on the desired mono-N-substituted diamine, which is unsatisfactory for industrial implementation.

There was therefore a need to provide a process which enabled the preparation of mono-N-sulphonated diamines in an efficient manner with good selectivities.

SUMMARY OF THE INVENTION

A process has now been found for preparing compounds of the formula (I), $$\text{H}_2\text{N}-\overset{R^1}{\underset{}{\diagup}}\overset{R^2}{\underset{}{\diagdown}}-\underset{H}{N}-SO_2R^3 \quad (I)$$

where
$R^1$ and $R^2$ are each independently $C_1$-$C_{20}$-alkyl, $C_4$-$C_{15}$-aryl or $C_5$-$C_{16}$-arylalkyl, or $R^1$ and $R^2$ together are a straight-chain or branched $C_3$-$C_{12}$-alkylene radical and
$R^3$ is $C_1$-$C_{20}$-alkyl, $C_1$-$C_{20}$-fluoroalkyl or $C_4$-$C_{15}$-aryl, which is characterized in that
diamines of the formula (II)

$$\text{H}_2\text{N}-\overset{R^1}{\underset{}{\diagup}}\overset{R^2}{\underset{}{\diagdown}}-NH_2 \quad (II)$$

where
$R^1$, $R^2$ and $R^3$ are as defined under formula (I)
are reacted
in the presence of water and
in the presence of organic solvents and
in the presence of a base with sulphonyl halides of the formula (III)

$$R^3SO_2X \quad (III)$$

where
X is fluorine, chlorine, bromine or iodine and
$R^3$ is as defined under formula (I).

DETAILED DESCRIPTION OF THE INVENTION

For the purposes of the invention, the radical definitions and illustrations listed in general or within areas of preference, i.e. the particular areas and areas of preference, may be combined as desired.

The compounds of the formula (I) and optionally the compounds of the formulae (II) and/or (III) are chiral. The invention explicitly encompasses both the pure stereoisomers (enantiomers and diastereomers) and any desired mixtures, for example racemates.

Preferably, $R^1$ and $R^2$ are identical and are each phenyl or are together straight-chain $C_3$-$C_8$-alkylene, for example 1,3-propylene or 1,4-butylene, and $R^1$ and $R^2$ are more preferably identical and are each phenyl.

$R^3$ is preferably $C_1$-$C_4$-alkyl, $C_1$-$C_4$-fluoroalkyl, phenyl or naphthyl, each of which may be further substituted by no, one, two, three, four or five radicals which are selected from the group of $C_1$-$C_4$-alkyl, $C_1$-$C_4$-alkoxy, $C_1$-$C_4$-fluoroalkyl, fluorine and chlorine.

$R^3$ is more preferably methyl, trifluoromethyl, pentafluoroethyl, nona-fluorobutyl, phenyl, p-tolyl, p-ethylphenyl, p-anisyl, p-ethoxyphenyl, p-chlorophenyl, 2,4,6-trimethylphenyl, 2,4,6-triisopropylphenyl, p-fluorophenyl, pentafluorophenyl and naphthyl.

$R^3$ is even more preferably p-tolyl, phenyl and naphthyl, and greatest preference is given to p-tolyl.

X is preferably fluorine or chlorine, more preferably chlorine.

Preference is given to using chiral compounds of the formula (II) which have an optical purity of 80% ee or more, more preferably a 90% ee or more and even more preferably a 98.5% ee or more.

The optical purity is defined as:

$$ee\ [S]=(m[S]-m[R])/m(S+R)$$

where
ee (S) is the optical purity of the enantiomer S, m(S) is the amount of the enantiomer S and m(R) is the amount of the enantiomer R. The enantiomeric excess is typically quoted in percent (% ee=ee/100).

The process according to the invention is especially suitable for the preparation of the following compounds of the formula (II):
N-[(1R,2R) and (1S,2S)-2-amino-1,2-diphenylethyl]-p-tolylsulphonamide, N-[(1R,2R) and (1S,2S)-2-amino-1,2-diphenylethyl]-o-tolylsulphonamide, N-[(1R,2R) and (1S,2S)-2-amino-1,2-diphenylethyl]-m-tolylsulphonamide, N-[(1R,2R) and (1S,2S)-2-amino-1,2-diphenylethyl]-phenylsulphonamide, N-[(1R,2R) and (1S,2S)-2-amino-1,2-diphenylethyl]-4-ethylphenylsulphonamide, N-[(1R,2R) and (1S,2S)-2-amino-1,2-diphenylethyl]-3-ethylphenylsulphonamide, N-[(1R,2R) and (1S,2S)-2-amino-1,2-diphenylethyl]-2-ethylphenylsulphonamide, N-[(1R,2R) and (1S,2S)-2-amino-1,2-diphenylethyl]-2,4,6-trimethylphenylsulphonamide, N-[(1R,2R) and (1S,2S)-2-amino-1,2-diphenylethyl]-2,4,6-triisopropylphenylsulphonamide, N-[(1R,2R) and (1S,2S)-2-amino-1,2- diphenylethyl]-4-chlorophenylsulphonamide, N-[(1R,2R) and (1S,2S)-2-amino-1,2-diphenylethyl]-3-chlorophenylsulphonamide, N-[(1R,2R) and (1S,2S)-2-amino-1,2-diphenylethyl]-2-chlorophenylsulphonamide, N-[(1R,2R) and (1S,2S)-2-amino-1,2-diphenylethyl]-4-fluorophenylsulphonamide, N-[(1R,2R) and (1S,2S)-2-amino-1,2-diphenylethyl]-3-fluorophenylsulphonamide, N-[(1R,2R) and (1S,2S)-2-amino-1,2-diphenylethyl]-2-fluorophenylsulphonamide, N-[(1R,2R) and (1S,2S)-2-amino-1,2-diphenylethyl]-4-methoxyphenylsulphonamide, N-[(1R,2R) and (1S,2S)-2-amino-1,2-diphenylethyl]-3-methoxyphenylsulphonamide, N-[(1R,2R) and (1S,2S)-2-amino-1,2-diphenylethyl]-2-methoxyphenylsulphonamide, N-[(1R,2R) and (1S,2S)-2-amino-1,2-diphenylethyl]-1-naphthylsulphonamide, N-[(1R,2R) and (1S,2S)-2-amino-1,2-diphenylethyl]-2-naphthylsulphonamide, N-[(1R,2R) and (1S,2S)-2-amino-1,2-diphenylethyl]-pentafluorophenylsulphonamide, N-[(1R,2R) and (1S,2S)-2-amino-1,2-diphenylethyl]-methanesulphonamide, N-[(1R,2R) and (1S,2S)-2-amino-1,2-diphenylethyl]-trifluoromethanesulphonamide, N-[(1R,2R) and (1S,2S)-2-aminocyclohexyl]-p-tolylsulphonamide, N-[(1R,2R) and (1S,2S)-2-aminocyclohexyl]-o-tolylsulphonamide, N-[(1R,2R) and (1S,2S)-2-aminocyclohexyl]-m-tolylsulphonamide, N-[(1R,2R) and (1S,2S)-2-aminocyclohexyl]-phenylsulphonamide, N-[(1R,2R) and (1S,2S)-2-aminocyclohexyl]-4-ethylphenylsulphonamide, N-[(1R,2R) and (1S,2S)-2-aminocyclohexyl]-3-ethylphenylsulphonamide, N-[(1R,2R) and (1S,2S)-2-aminocyclohexyl]-2-ethylphenylsulphonamide, N-[(1R,2R) and (1S,2S)-2-aminocyclohexyl]-2,4,6-trimethylphenylsulphonamide, N-[(1R,2R) and (1S,2S)-2-aminocyclohexyl]-2,4,6-triisopropylphenylsulphonamide, N-[(1R,2R) and (1S,2S)-2-aminocyclohexyl]-4-chlorophenylsulphonamide, N-[(1R,2R) and (1S,2S)-2-aminocyclohexyl]-3-chlorophenylsulphonamide, N-[(1R,2R) and (1S,2S)-2-aminocyclohexyl]-2-chlorophenylsulphonamide, N-[(1R,2R) and (1S,2S)-2-aminocyclohexyl]-4-fluorophenylsulphonamide, N-[(1R,2R) and (1S,2S)-2-aminocyclohexyl]-3-fluorophenylsulphonamide, N-[(1R,2R) and (1S,2S)-2-aminocyclohexyl]-2-fluorophenylsulphonamide, N-[(1R,2R) and (1S,2S)-2-aminocyclohexyl]-4-methoxyphenylsulphonamide, N-[(1R,2R) and (1S,2S)-2-aminocyclohexyl]-3-methoxyphenylsulphonamide, N-[(1R,2R) and (1S,2S)-2-aminocyclohexyl]-2-methoxyphenylsulphonamide, N-[(1R,2R) and (1S,2S)-2-aminocyclohexyl]-1-naphthylsulphonamide, N-[(1R,2R) and (1S,2S)-2-aminocyclohexyl]-2-naphthylsulphonamide, N-[(1R,2R) and (1S,2S)-2-aminocyclohexyl]-pentafluorophenylsulphonamide, N-[(1R,2R) and (1S,2S)-2-aminocyclohexyl]-methanesulphonamide, N-[(1R,2R) and (1S,2S)-2-aminocyclohexyl]-trifluoromethanesulphonamide, N-[(1R,2R) and (1S,2S)-2-aminocyclopentyl]-p-tolylsulphonamide, N-[(1R,2R) and (1S,2S)-2-aminocyclopentyl]-o-tolylsulphonamide, N-[(1R,2R) and (1S,2S)-2-aminocyclopentyl]-m-tolylsulphonamide, N-[(1R,2R) and (1S,2S)-2-aminocyclopentyl]-phenylsulphonamide, N-[(1R,2R) - and (1S,2S)-2-aminocyclopentyl]-4-ethylphenylsulphonamide, N-[(1R,2R) and (1S,2S)-2-aminocyclopentyl]-3-ethylphenylsulphonamide, N-[(1R,2R) and (1S,2S)-2-aminocyclopentyl]-2-ethylphenylsulphonamide, N-[(1R,2R) and (1S,2S)-2-aminocyclopentyl]-2,4,6-trimethylphenylsulphonamide, N-[(1R,2R) and (1S,2S)-2-aminocyclopentyl]-2,4,6-triisopropylphenylsulphonamide, N-[(1R,2R) and (1S,2S)-2-aminocyclopentyl]-4-chlorophenylsulphonamide, N-[(1R,2R) and (1S,2S)-2-aminocyclopentyl]-3-chlorophenylsulphonamide, N-[(1R,2R) and (1S,2S)-2-aminocyclopentyl]-2-chlorophenylsulphonamide, N-[(1R,2R) and (1S,2S)-2-aminocyclopentyl]-4-fluorophenylsulphonamide, N-[(1R,2R) and (1S,2S)-2-aminocyclopentyl]-3-fluorophenylsulphonamide, N-[(1R,2R) and (1S,2S)-2-aminocyclopentyl]-2-fluorophenylsulphonamide, N-[(1R,2R) and (1S,2S)-2-aminocyclopentyl]-4-methoxyphenylsulphonamide, N-[(1R,2R) and (1S,2S)-2-aminocyclopentyl]-3-methoxyphenylsulphonamide, N-[(1R,2R) and (1S,2S)-2-aminocyclopentyl]-2-methoxyphenylsulphonamide, N-[(1R,2R) and (1S,2S)-2-aminocyclopentyl]-1-naphthylsulphonamide, N-[(1R,2R) and (1S,2S)-2-aminocyclopentyl]-2-naphthylsulphonamide, N-[(1R,2R) and (1S,2S)-2-aminocyclopentyl]-pentafluorophenylsulphonamide, N-[(1R,2R) and (1S,2S)-2-aminocyclopentyl]-methanesulphonamide and N-[(1R,2R) and (1S,2S)-2-aminocyclopentyl]-trifluoromethanesulphonamide or mixtures of the particular enantiomers, in particular the racemates.

The process according to the invention is carried out in the presence of water, base and organic solvent. Examples of suitable organic solvents are: amides, e.g. dimethylformamide, N-methylpyrrolidinone, optionally halogenated aliphatic or aromatic solvents having up to 16 carbon atoms, e.g. toluene, o-, m-, p-xylene, carbon tetrachloride, chloroform, dichloromethane, chlorobenzene, the isomeric dichlorobenzenes, fluorobenzene, nitriles, e.g. acetonitrile and benzonitrile, sulphoxides such as dimethyl sulphoxide or mixtures thereof.

Advantageously, the organic solvents are selected in such a way that the reaction mixture forms two liquid phases. Particularly suitable solvents for this purpose are optionally halogenated aliphatic or aromatic solvents having up to 16 carbon atoms, and preference is given to carbon tetrachloride, chloroform, dichloromethane and chlorobenzene, even greater preference to dichloromethane.

The volume ratio of water to organic solvents can be, for example, 20:1 to 1:20, preferably a ratio of 10:1 to 1:10 and more preferably a ratio of 5:1 to 1:5.

In a preferred embodiment, the process according to the invention is carried out in such a way that the reaction mixture forms two liquid phases and the aqueous phase has a pH at 25° C. of 8 or more, preferably 11 to 14.

The pH is adjusted by the use of a base.

Examples of useful bases are alkali metal and alkaline earth metal hydroxides and carbonates, more preferably potassium hydroxide and sodium hydroxide.

The total molar amount of the base used can be, for example, 1 to 10 equivalents, based on the diamine of the formula (II) used, preferably 1.1 to 3 equivalents. Larger amounts of base are possible but uneconomic.

The entire amount of base may be added from the beginning onwards or at least partially in the course of the reaction.

The molar ratio of compound of the formula (II) to compounds of the formula (III) can, for example, be 0.1 to 1.3 equivalents, preferably 0.5 to 1.3 equivalents, more preferably 0.8 to 1.1 equivalents, even more preferably 0.99 to 1.03 equivalents. The temperature in the reaction can be, for example, −30 to 100° C., preferably −20 to 50° C. and more preferably 0 to 30° C.

The reaction time can be, for example, 10 minutes to 24 hours, preferably 30 min to 2 h.

In cases where the reaction mixture comprises two liquid phases, it is particularly advantageous to ensure sufficient mixing. This may be effected, for example, by vigorous stirring.

The products may be isolated from the reaction solution, for example, by conversion to the hydrohalide, crystallization or precipitation of the hydrohalides and release of the compound of the formula (I) from the hydrohalide using base.

The conversion to the hydrohalide, preferably the hydrochloride, can advantageously be effected by reacting the reaction solution with aqueous hydrohalic acid, preferably aqueous hydrochloric acid.

Alternatively, the compounds of the formula (I) may also be further purified by crystallization from a suitable solvent or solvent mixture or from the reaction solution or by chromatography.

It has proven particularly advantageous to use the reaction solutions preferably by the process according to the invention directly and without further purification after removing the aqueous phase and optionally drying the organic phase.

The invention therefore also encompasses solutions comprising compounds of the formula (I)

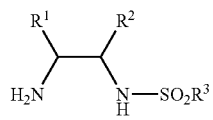
(I)

where
$R^1$ and $R^2$ are each independently $C_1$-$C_{20}$-alkyl, $C_4$-$C_{15}$-aryl or $C_5$-$C_{16}$-arylalkyl, or $R^1$ and $R^2$ together are a straight-chain or branched $C_3$-$C_{12}$-alkylene radical and
$R^3$ is $C_1$-$C_{20}$-alkyl, $C_1$-$C_{20}$-fluoroalkyl or $C_4$-$C_{15}$-aryl, which are obtainable by
a) reacting compounds of the formula (II)

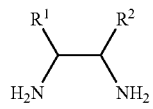
(II)

where
$R^1$, $R^2$ and $R^3$ are as defined under formula (I)
in the presence of water and
in the presence of organic solvents and
in the presence of a base
with sulphonyl halides of the formula (III)

$R^3SO_2X$ (III)

where
X is fluorine, chlorine, bromine or iodine and
$R^3$ is as defined under formula (I) and
b) at least partly removing water.

Preference is given to effecting the reaction in a reaction mixture which forms two liquid phases. In this case, water can be removed, for example, by removing the aqueous phase and optionally subsequently drying the organic phase.

Drying methods for organic phases are sufficiently well known to those skilled in the art and include, for example, azeotropic distillation, optionally under reduced pressure, drying over sodium sulphate or magnesium sulphate, molecular sieves and other drying agents inert towards organic solvents and subsequent filtration.

The solutions according to the invention preferably have a water content of 2% by volume or less, preferably 1% or less.

The solutions according to the invention comprising the compounds of the formula (I) and also the compounds of the formula (I) preparably according to the invention are suitable in particular for use in catalysis, in particular homogeneous catalysis, or for preparing metal complexes, in particular transition metal complexes.

The solutions according to the invention comprising the compounds of the formula (I) and also the compounds of the formula (I) preparably according to the invention are especially suitable for preparing ruthenium, rhodium or iridium complexes and for use in hydrogenations, in particular for hydrogenating imines and ketones in the presence of ruthenium, rhodium or iridium complexes, hydrogen donors and bases, known as transfer hydrogenation. Examples of typical hydrogen donors are formic acid and isopropanol, examples of typical bases are alkali metal hydroxides and amines, in particular triethylamine.

A review of transfer hydrogenations as a method for catalytic reduction is given, for example, by Zassinovich et al. in Chem. Rev. 1992, 92, 1051-1069 and Noyori et al. in Acc. Chem. Res. 1997, 30, 97-102 and Wills et al. in Tetrahedron, Asymmetry, 1999, 2045.

The invention also encompasses catalysts obtainable by
a) reacting compounds of the formula (II)

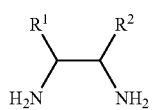
(II)

where
$R^1$ and $R^2$ are each independently $C_1$-$C_{20}$-alkyl, $C_4$-$C_{15}$-aryl or $C_5$-$C_{16}$-arylalkyl, or $R^1$ and $R^2$ together are a straight-chain or branched $C_3$-$C_{12}$-alkylene radical
in the presence of water and
in the presence of organic solvents and
in the presence of a base
with sulphonyl halides of the formula (III)

$R^3SO_2X$ (III)

where
X is fluorine, chlorine, bromine or iodine and
$R^3$ is $C_1$-$C_{20}$-alkyl, $C_1$-$C_{20}$-fluoroalkyl or $C_4$-$C_{15}$-aryl,
b) at least partly removing water and
c) reacting the solution obtained in step b)
with compounds of the formula (IV)

$[MX_n(R^4)]_2$ (IV)

where
M is ruthenium, rhodium or iridium,
$R^4$ is an aromatic compound which has 6 to 12 ring carbon atoms and may be substituted by up to 6 radicals which are each independently selected from the group of $C_1$-$C_8$-alkyl, benzyl and phenyl, or cyclopentadienyl or indenyl, each of which are substituted by up to five radicals, and X is, for example and with preference, chlorine, bromine or iodine, more preferably chlorine, and n is two where M is ruthenium, n is one where M is rhodium or iridium, optionally and preferably in the presence of a tertiary amine.

Preference is given to effecting the reaction in a reaction mixture which forms two liquid phases. In this case, water can be removed, for example, by removing the aqueous phase and optionally drying the organic phase.

For example and with preference, the compounds of the formula (IV) used are those in which M is ruthenium and n is two.

In the compounds of the formula (IV), $R^4$ is preferably benzene or naphthalene, each of which may be substituted by one, two, three, four, five or six radicals which are each independently selected from the group of methyl, ethyl, n-propyl, isopropyl and tert-butyl, or is pentamethylcyclopentadienyl. $R^4$ in compounds of the formula (IV) is preferably mesitylene, benzene or cumene.

Compounds of the formula (IV) include: (benzene)dichlororuthenium dimer, (mesitylene)dichlororuthenium dimer, (cumene)dichlororuthenium dimer, (pentamethylcyclopentadienyl) (chloro) (chloro)rhodium dimer and (pentamethylcyclopentadienyl)(chloro)iridium dimer.

For the purposes of the invention, a particularly preferred compound of the formula (IV) is (cumene)dichlororuthenium dimer.

In a preferred embodiment, the molar ratio of compound of the formula (II) originally used to compounds of the formula (IV) is 2:1 to 3:1, more preferably 2.2:1 to 2.6:1.

The catalysts according to the invention are preferably suitable for use in hydrogenations, in particular for hydrogenating imines and ketones in the presence of hydrogen donors and bases, known as transfer hydrogenation.

The advantage of the invention is that the compounds of the formula (I) can be obtained in high yield and very good selectivity. It has also been found that the products of the sulphonylation can be used for the preparation of catalysts without intermediate isolation, which constitutes a considerable simplification in industrial use.

The invention is further described by the following illustrative but non-limiting examples.

EXAMPLES

Example 1

In a 3-necked flask, 5.0 g of S,S-diphenylethylenediamine are dissolved in 40 ml of $CH_2Cl_2$. Subsequently, 40 ml of 1 M sodium hydroxide solution are added and the mixture is cooled by means of an ice bath. Afterwards, a solution of 4.49 g of p-toluenesulphonyl chloride in 80 ml of $CH_2C_2$ are added dropwise at 0° C. within 60 min. After 1 h at 0° C., the reaction is terminated. The organic phase is removed and washed with water, and the solvent is removed on a rotary evaporator. Crude diamine:mono-: disubstitution product: 3.5:93:3.5.

Crystallization is effected from toluene: hexane.

Yield: 7.8 g of crystalline product (91%), mono-: disubstitution product selectivity: 95.5:4.5.

Example 2 (For Comparison)

In a 3-necked flask, 2.21 g of p-toluenesulphonyl chloride in 40 ml of $CH_2Cl_2$ are admixed with 3.0 ml of triethylamine (1.8 eq). The mixture is cooled to 0° C. and 2.46 g of S,S-diphenyethylenediamine are added. After 1 h at 0° C. and 4 h at RT, the reaction is worked up. The mixture is diluted with 50 ml of dichloromethane and washed with 50 ml of 0.5 M NaOH, the cloudy organic phase is removed and washed with 20 ml of water and 50 ml of NaCl solution and the solvent is removed on a rotary evaporator. The mixture is admixed with toluene and remaining triethylamine is removed azeotropically.

Yield: 2.93 g ("69%") of crude product, mono-: disubstitution product selectivity: 83:17.

Example 3

In a 3-necked flask, 2.0 g of S,S-diphenylethylenediamine are dissolved in 20 ml of $CH_2Cl_2$. Subsequently, 10 ml of 2 M sodium hydroxide solution are added and the mixture is cooled by means of an ice bath. Afterwards, a solution of 2.08 g of mesitylsulphonyl chloride in 20 ml of $CH_2Cl_2$ are added dropwise at 0° C. within 20 min. After 1 h at 0° C., the reaction is worked up. The organic phase is removed and washed with water and sodium chloride solution, and the solvent is removed on a rotary evaporator. The residue of 3.9 g shows a diamine:mono-:disubstitution product selectivity of 1.7:92:6.5.

Recrystallization from toluene/hexane results in 3.1 g of crystalline product (83%), mono-:disubstitution product selectivity: 94.8:5.2.

Example 4 (For Comparison)

In a 3-necked flask, 2.0 g of S,S-diphenylethylenediamine are dissolved in 20 ml of $CH_2Cl_2$, 1.98 ml of $Et_3N$ (1.5 eq) are added and the mixture is cooled to 0° C. A solution of 2.08 g of mesitylsulphonyl chloride in 20 ml of $CH_2Cl_2$ is added dropwise at this temperature within 20 min. The mixture is thawed to room temperature within one hour. It is washed with 20 ml of water and 50 ml of NaCl solution and the solvent is removed on a rotary evaporator. The residue is admixed with toluene and remaining triethylamine is removed azeotropically.

Mono:disubstitution product selectivity 84:16.

Example 5

In a 3-necked flask, 2.0 g of S,S-diphenylethylenediamine are dissolved in 20 ml of $CH_2Cl_2$. Subsequently, 10 ml of 2 M sodium hydroxide solution are added and the mixture is cooled by means of an ice bath. Afterwards, a solution of 1.68 g of phenylsulphonyl chloride in 20 ml of $CH_2Cl_2$ are added dropwise at 0° C. within 20 min. After 1 h at 0° C., the reaction is stirred at room temperature for a further 12 h. The organic phase is removed and washed with water and sodium chloride solution, and the solvent is removed on a rotary evaporator. The residue of 3.1 g shows a diamine: mono-:disubstitution product selectivity of 2:94:4.

Recrystallization from toluene/hexane results in 2.9 g of crystalline product (87%), mono-:disubstitution product selectivity: 95:5.

Example 6 (For Comparison)

In a 3-necked flask, 2.0 g of S,S-diphenylethylenediamine are dissolved in 20 ml of $CH_2Cl_2$, 1.98 ml of $Et_3N$ (1.5 eq) are added and the mixture is cooled to 0° C. A solution of 1.68 g of phenylsulphonyl chloride in 20 ml of $CH_2Cl_2$ is added dropwise at this temperature within 20 min. The mixture is thawed to RT within one hour and stirred at room temperature for a further 12 h. It is washed with 20 ml of water and 50 ml of NaCl solution and the solvent is removed on a rotary evaporator. The residue is admixed with toluene and remaining triethylamine is removed azeotropically.

Mono:disubstitution product selectivity: 91:9.

Example 7

In a 3-necked flask, 1.0 g of S,S-diphenylethylenediamine are dissolved in 20 ml of $CH_2Cl_2$. Subsequently, 10 ml of 1 M sodium hydroxide solution are added and the mixture is cooled by means of an ice bath. Afterwards, a solution of 0.70 g of pentafluorosulphonyl chloride in 20 ml of $CH_2Cl_2$ are added dropwise at 0° C. within 20 min. After 1 h at 0° C., the reaction is stirred at room temperature for a further 12 h. The organic phase is removed and washed with water and sodium chloride solution, and the solvent is removed on a rotary evaporator. 1.5 g of crystalline product (72%) are isolated, mono-:disubstitution product selectivity: 83:17.

Example 8 (For Comparison)

In a 3-necked flask, 1.0 g of S,S-diphenylethylenediamine is dissolved in 20 ml of $CH_2Cl_2$, 0.99 ml of $Et_3N$ (1.5 eq) is added and the mixture is cooled to 0° C. A solution of 0.70 g of pentafluorophenylsulphonyl chloride in 20 ml of $CH_2Cl_2$ is added dropwise at this temperature within 20 min. The mixture is thawed to RT within one hour and stirred at room temperature for a further 12 h. It is washed with 20 ml of water and 50 ml of NaCl solution and the solvent is removed on a rotary evaporator. The residue is admixed with toluene and remaining triethylamine is removed azeotropically.

Mono:disubstitution product selectivity 76:24.

Example 9

Preparation of a catalyst stock solution in situ without isolating the ligand

In a Schlenk flask, 0.4 g of S,S-diphenylethylenediamine is dissolved in 10 ml of $CH_2Cl_2$. Subsequently, 4 ml of 1 M sodium hydroxide solution are added and the mixture is cooled by means of an ice bath. Afterwards, a solution of 0.36 g of tosyl chloride in 10 ml of $CH_2Cl_2$ is added dropwise at 0° C. with vigorous stirring within 10 min. After 1 h at 0° C., the phases are separated. The organic phase is removed and washed with water and NaCl solution.

The ligand solution prepared in this way is degassed and stirred in a Schlenk vessel with 0.56 g of $[(cumene)RuCl_2]_2$ (=0.44 mol equivalent based on the S,S-diphenylethylenediamine) and 550 μl of $Et_3N$ for 20 min.

Example 10

Half of the catalyst solution prepared in Example 9 is used for this experiment. In a 500 ml four-necked flask equipped with sparging stirrer, reflux condenser and thermometer, a formic acid/$Et_3N$ mixture is prepared from 70 ml of triethylamine and 20 ml of HCOOH by slowly adding HCOOH dropwise to the $Et_3N$ by dropping funnel within 5 min with stirring and ice cooling. 76 g of methyl 3-keto-3-(2-thiophenyl)propanoate (S/C=500) are added to this biphasic mixture, the homogeneous yellow solution is admixed with 50 ml of dichloromethane and the overall mixture is degassed by passing argon through for 20 min. The mixture is heated to 40° C. and half of the catalyst solution from Example 5 is added all at once to the reaction mixture by syringe with vigorous stirring. The mixture is stirred while passing argon through for 18 h, then the reaction solution is diluted with water and $CH_2Cl_2$, the mixture is stirred for a further 10 min, and the $H_2O$ phase is extracted twice using $CH_2Cl_2$ after phase separation. The combined organic phases are washed with water and NaCl solution, dried over $MgSO_4$ and filtered, and then the solvent is removed on a rotary evaporator. 75 g of methyl 3-S-hydroxy-3-(2-thiophenyl)propanoate are obtained (97.7%).

Conversion (GC): 99.9%. ee (chiral GC, IVADEX 3): 97.2%.

Example 11 (For Comparison)

Procedure as Example 10, except that the catalyst used is 0.52 g of independently prepared [N-[(1R,2R)-2-(amino-κN)-1,2-diphenylethyl]-p-tolylsulphonamidato-κN]chloro[($\eta^6$)-cumene]ruthenium(II). The mixture is stirred for 18 h and subsequently worked up as described in Example 6.75 g of methyl 3-R-hydroxy-3-(2-thiophenyl)propanoate are obtained (97.7%).

Conversion: 99.5%. ee: 96.9%.

Example 12

In a 250 ml four-necked flask equipped with sparging stirrer, reflux condenser and thermometer, a formic acid/$Et_3N$ mixture is prepared from 41 ml of triethylamine and 12 ml of HCOOH by slowly adding HCOOH dropwise to the $Et_3N$ by dropping funnel with stirring and ice cooling. 49.5 g of 4-bromoacetophenone (S/C=300) are added to this biphasic mixture, the homogeneous yellow solution is admixed with 30 ml of dichloromethane and the overall mixture is degassed by passing through argon for 20 min. Half of the catalyst solution from Example 9 is added all at once to the reaction mixture by pipette with vigorous stirring at room temperature. The mixture is stirred while passing argon through for 18 h, subsequently the reaction solution is diluted with water and $CH_2Cl_2$, the mixture is stirred for a further 10 min, and the $H_2O$ phase is extracted twice using $CH_2Cl_2$ after phase separation. The combined organic phases are washed with NaCl solution, dried over $MgSO_4$ and filtered, and then the solvent is removed on a rotary evaporator. The conversion is 99.5% (GC). ee (chiral GC): 93.9%.

The oily, viscose residue is mixed with a little hexane and crystallized at −20° C. In the first crystals, 23 g (46%) of the white crystalline product are obtained. p-Bromo-1-phenylethan-1-ol (ee:>99%).

Example 13 (For Comparison)

The procedure was similar to Example 12, with the difference that the substrate used was 4.98 g of 4-bromoacetophenone and the catalyst used was 31 mg of [N-[(1R,2R)-2-(amino-κN)-1,2-diphenylethyl]-p-tolylsulphonamidato-κN]chloro[($\eta^6$)-1,3,5-trimethylbenzene]ruthenium(II).

After a reaction time of 48 h (not optimized), >99% conversion is achieved. The crude product has an enantiomeric excess of 95.3%. Crystallization at −20° C. from hexane results in purification to >99% enantiomeric excess.

Example 14

In a 250 ml four-necked flask equipped with sparging stirrer, reflux condenser and thermometer, a formic acid/$Et_3N$ mixture is prepared from 41 ml of triethylamine and 12 ml of HCOOH by slowly adding HCOOH dropwise to the Et₃N by dropping funnel within 5 min with stirring and ice cooling. 49.5 g of 4-bromoacetophenone (S/C 300) are added to this 2-phase mixture, the homogeneous yellow solution is admixed with 30 ml of dichloromethane and the overall mixture is degassed by passing argon through for 20 min. The mixture is heated to 25° C. and a catalyst solution prepared in a similar manner to Example 9 (half batch) is added all at once to the reaction mixture by syringe with vigorous stirring. The mixture is stirred under argon for 18 h, the reaction solution is diluted with water and CH₂Cl₂, the mixture is stirred for a further 10 min, and the H₂O phase is extracted twice using CH₂Cl₂ after phase separation. The combined organic phases are washed with NaCl solution, dried over MgSO₄ and filtered, and then the solvent is removed on a rotary evaporator. The conversion is 99.8% (GC). ee (chiral GC): 92.6%.

The residue is dissolved in hexane and crystallized at −20° C. In the first crystals, 35 g (70%) of the white crystalline product 2-bromo-1-phenylethan-1-ol (ee: >99.5%) are obtained.

What is claimed is:

1. Process for preparing compounds of the formula (I),

(I)

where
R¹ and R² are each independently $C_1$-$C_{20}$-alkyl, $C_4$-$C_{15}$-aryl or $C_5$-$C_{16}$-arylalkyl, or R¹ and R² together are a straight-chain or branched $C_3$-$C_{12}$-alkylene radical arid
R³ is $C_1$-$C_{20}$-alkyl, $C_1$-$C_{20}$-fluoroalkyl or $C_4$-$C_{15}$-aryl,
comprising reacting
diamines of the formula (II)

(II)

where
R¹, R² and R³ are as defined under formula (I)
in the presence of water and
in the presence of organic solvent and
in the presence of a base comprising alkali metal, alkaline earth metal hydroxide, or carbonate,
with sulphonyl halides of the formula (III)

R³SO₂X                                (III)

where
X is fluorine, chlorine, bromine or iodine and
R³ is as defined under formula (I).

2. Process according to claim 1, characterized in that R¹ and R² are identical and are each phenyl or are together straight-chain $C_3$-$C_8$-alkylene.

3. Process according to claim 1, characterized in that R³ is $C_1$-$C_4$-alkyl, $C_1$-$C_4$-fluoroalkyl, phenyl or naphthyl, each of which is optionally further substituted by no, one, two, three, four or five radicals which are selected from the group of $C_1$-$C_4$-alkyl, $C_1$-$C_4$-alkoxy, $C_1$-$C_4$-fluoroalkyl, fluorine and chlorine.

4. Process according to claim 1, characterized in that X is fluorine or chlorine.

5. Process according to claim 1, characterized in that chiral compounds of the formula (II) are used which have an optical purity of 80% ee or more.

6. Process according to claim 1, characterized in that the organic solvent used is selected from the group consisting of an amide, an optionally halogenated aliphatic or aromatic solvent having up to 16 carbon atoms, a nitrile, a sulphoxide or a mixture thereof.

7. Process according to claim 1, characterized in that the organic solvent used is carbon tetrachloride, chloroform, dichloromethane or chlorobenzene.

8. Process according to one claim 1, characterized in that the volume ratio of water to organic solvent is 20:1 to 1:20.

9. Process according to claim 1, characterized in that the reaction mixture forms two liquid phases and the aqueous phase has a pH at 25° C. of 8 or more.

10. Process according to claim 1, characterized in that the molar ratio of compounds of the formula (II) to compounds of the formula (III) is 0.5 to 1.3.

11. Process according to claim 1, further characterized in that the products are isolated from the reaction solution, by conversion into the hydrohalide, crystallization or precipitation of the hydrohalide and release of the compound of the formula (I) from the hydrohalide using base.

* * * * *